United States Patent [19]
Mizuno et al.

[11] Patent Number: 5,252,400
[45] Date of Patent: Oct. 12, 1993

[54] FLUORINE-CONTAINING COMPOUNDS

[75] Inventors: Naoko Mizuno; Yoshiaki Kai, both of Neyagawa; Takashi Suzuki, Takatsuki, all of Japan

[73] Assignee: Matsushita Electric Industrial Co., Ltd., Osaka, Japan

[21] Appl. No.: 757,941

[22] Filed: Sep. 12, 1991

[30] Foreign Application Priority Data

Nov. 13, 1990 [JP] Japan ................................. 2-307391
Nov. 21, 1990 [JP] Japan ................................. 2-319004

[51] Int. Cl.$^5$ ............................................. B32B 27/00
[52] U.S. Cl. ...................................... 428/421; 252/50; 252/51; 252/58; 428/695; 428/900; 562/567; 562/849; 562/850
[58] Field of Search ............... 428/421, 422, 695, 900; 252/50, 51, 58; 562/567, 849, 850; 528/372; 106/14.18

[56] References Cited

U.S. PATENT DOCUMENTS

| | | | |
|---|---|---|---|
| 3,778,308 | 12/1973 | Roller et al. | 428/421 |
| 3,798,265 | 3/1974 | Bartlett | 562/567 |
| 4,268,556 | 5/1981 | Pedrotty | 428/65 |
| 4,526,833 | 7/1985 | Burguette et al. | 428/336 |
| 4,696,845 | 9/1987 | Yanagisawa | 428/64 |
| 4,898,683 | 2/1990 | Dekura | 252/51 |

FOREIGN PATENT DOCUMENTS

| | | |
|---|---|---|
| 0152784 | 8/1985 | European Pat. Off. . |
| 0296046 | 12/1988 | European Pat. Off. . |
| 0296935 | 12/1988 | European Pat. Off. . |
| 60-109028 | 6/1985 | Japan . |
| 61-107527 | 5/1986 | Japan . |
| 61-107528 | 5/1986 | Japan . |
| 61-107529 | 5/1986 | Japan . |
| 62-92225 | 4/1987 | Japan . |
| 62-92226 | 4/1987 | Japan . |
| 62-92227 | 4/1987 | Japan . |

OTHER PUBLICATIONS

Kondo, et al. "Perfluoroalkylcarboxylic Acid Amine Salts as Lubricants and Magnetic Recording Medium Using Them," Chemical Abstracts, vol. 110, No. 20, p. 199; col. 2, May 15, 1989.

Primary Examiner—Paul J. Thibodeau
Assistant Examiner—Hoa T. Le
Attorney, Agent, or Firm—Stevens, Davis, Miller & Mosher

[57] ABSTRACT

Disclosed in this invention are novel fluorine-contianing compounds of a specific molecular structure having a fluoroalkylether terminal group, an aliphatic hydrocarbon terminal group and an imino terminal group in the same molecule and a molecular weight of from several hundred to about 3,000, and a process for preparing such compounds. The fluorine-containing compounds of this invention can be utilized as a lubricant composition for magnetic recording media.

3 Claims, 1 Drawing Sheet

FLUORINE-CONTAINING COMPOUNDS

BACKGROUND OF THE INVENTION

1. Field of the Invention

This invention relates to novel fluorine-containing compounds useful as lubricants for precision machines and precision parts which require high-precision lubrication, and, as other chemical agents such as surfactants, releasing agents, rust preventives, etc., a process for preparing such fluorine-containing compounds, lubricant compositions containing said fluorine-containing compounds, and the magnetic recording media such as magnetic tapes, magnetic discs, etc., containing said fluorine-containing compounds in a lubricant layer.

2. Description of Prior Art

With the progressive tendency toward miniaturization and higher precision of machines and parts, the type of lubrication at sliding sections is being converted from fluid lubrication into boundary lubrication. Especially in the electronic machines and parts such as VTR, magnetic discs, etc., high-precision lubrication is required for the sliding motion between the magnetic tape or disc and the magnetic head because of the employment of thin ferromagnetic metal films purposed for improving recording density. For instance, in the deposited tapes or hard discs, in order to attain a maximum output by minimizing spacing loss between the magnetic recording medium and the magnetic head while securing the required durability and practical reliability, the lubricant layer formed at the surface of the magnetic layer is allowed to have a thickness of only several tens of Å. Hence, development of an organic compound with excellent lubricating performance as a material for forming said lubricant layer is now an important subject for study in the art.

As the lubricants for the thin metal film type magnetic recording media, many fluorocarbon type lubricants have been proposed in view of the fact that the lubricants having a fluorocarbon chain in the molecule have good compatibility with the thin metal films (see, for example, Japanese Patent Application Kokai (Laid-Open) Nos. 61-107527, 61-107528, 61-107529, 62-92225, 62-92226 and 62-92227). Proposals have also been made for lubricants for magnetic recording media prepared by using a compound comprising perfluoroalkyl-polyether chains (see, for example, U.S. Pat. No. 3,778,308 and JPN Pat. Appln. Kokai No. 60-109028).

On the other hand, as a preparation having a similar molecular structure to the fluorine-containing compounds of this invention, there has been proposed a surfactant having the following molecular structure:

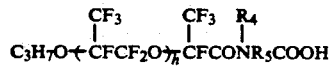

wherein $R_4$ is hydrogen atom or an aliphatic alkyl group having 1-12 carbon atoms; $R_5$ is an aliphatic alkylene group having 1, 2 or 5 carbon atoms; and h is an integer of 0 to 8 (U.S. Pat. No. 3,798,265).

It is imperative that a lubricant for thin metal film type magnetic recording media adheres strongly to the surface of thin metal film or protective film and the surface of the magnetic head to form the lubricant coating layers on said surfaces and is easily sheared between the lubricant molecules at the contact area of said coating layers, namely at the sliding area between the magnetic recording medium and the magnetic head. The perfluoroalkylpolyethers which have been used as lubricants for the magnetic recording media have good intermolecular shearing characteristics since the molecule surface is almost entirely covered with fluorine atoms, but they are weak in adhesive force to the surface of the thin metal film or protective film and the surface of magnetic head because of the weak polarity of their molecules. In order to overcome this defect, it has been proposed to introduce various types of polar group to the molecular terminals of perfluoroalkylpolyethers. However, when the molecular weight of the perfluoroalkylpolyether is greater than 3,000, the effect of introduction of a polar group is insufficient, and when the molecular weight is reduced for enhancing the effect of the polar group, there results a decrease in the amount of the lubricant due to its own evaporation because of the reduced intermolecular action of the perfluoroalkylpolyether. Thus, the perfluoroalkylpolyethers and their terminal-modified version were poor in adhesiveness to the thin metal film or protective film surface and the magnetic head surface and in stability, so that the lubricants prepared by using said compounds, especially those for thin metal film type magnetic recording media had the problems over durability and reliability, especially over use quality or performance under a low-humidity environment where cohesion of magnetic metal tends to occur at the magnetic head surface.

On the other hand, the fluorocarbon type lubricants disclosed in the afore-mentioned prior references have been applied to the thin metal film type magnetic recording media because of their good compatibility with thin metal films, but they are unsatisfactory in durability under an environment of a low humidity below 10% RH.

Here, a review is given of the prior references disclosing the processes resembling the fluorine-containing compound preparation process of this invention or the processes for preparing the compounds resembling the fluorine-containing compounds provided according to the present invention.

A process for preparing the compounds resembling the fluorine-containing compounds of the present invention is proposed in Japanese Patent Application Kokai No. 64-26539. The process of this prior application comprises hydrogenating a mixture of an unsaturated secondary amino-alcohol and a saturated secondary amino-alcohol and subjecting the resulting product to an epoxylation or esterification reaction to obtain a polyfluorinated amino-alcohol or an ester thereof.

According to this process, it is impossible to obtain a single fluorinated compound; the product is a mixture of the three fluorinated compounds with different molecular structures. Also, to obtain the fluorinated compounds with high purity, it is necessary to conduct purification with a silica column or other means, which leads to an elevated production cost.

SUMMARY OF THE INVENTION

The object of the present invention is to provide novel fluorine-containing compounds which are capable of affording satisfactory durability to the thin metal film type magnetic recording media under all possible use conditions including harsh low-humidity environments, lubricant compositions containing said fluorine-containing compounds, and the magnetic recording media such as magnetic tapes, magnetic discs, etc., having one of said fluorine-containing compounds contained in the lubricant layer.

As a result of extensive studies pursued for overcoming said problems of the prior art and for attaining the above-said object, the present inventors have reached the conclusion that a fluorine-containing compound having a fluoroalkylether terminal group, an aliphatic hydrocarbon terminal group and a specific polar terminal group in the same molecule is best suited as a lubricant for the thin metal film type magnetic recording media. The present invention was achieved on the basis of this conclusion and the finding of a novel compound preparation process.

Thus, the present invention relates to the novel fluorine-containing compounds represented by the formula:

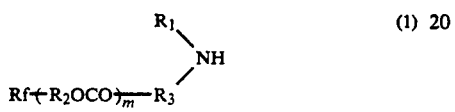
(1)

(wherein Rf represents a fluoroalkylether terminal group having 5-50 carbon atoms; $R_1$ represents an aliphatic alkyl terminal group or an aliphatic alkenyl terminal group; $R_2$ and $R_3$ represent an alkylene group; and m is 0 or 1), and a process for preparing such fluorine-containing compounds.

Figure 1:
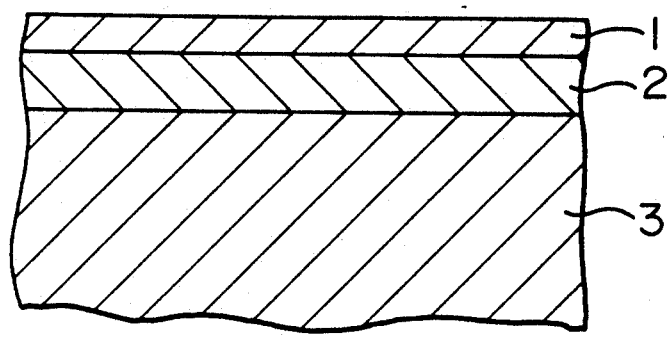
FIG. 1 is a schematic sectional view of a thin ferromagnetic metal film type magnetic recording medium having a lubricant layer formed directly on a magnetic layer. In the drawing, reference numeral 1 denotes a lubricant layer containing a compound of this invention. This lubricant layer 1 is formed on the surface of a magnetic layer 2 formed on a non-magnetic support 3.
Figure 2:
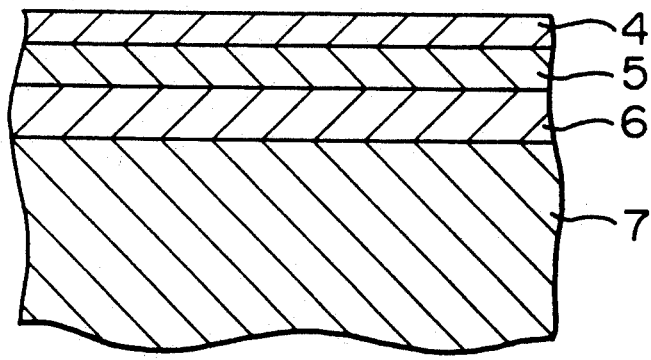
FIG. 2 is a schematic sectional view of a thin ferromagnetic metal film type magnetic recording medium having a lubricant layer formed on a magnetic layer with a protective film interposed therebetween. In the drawing, reference numeral 4 indicates a lubricant layer containing a compound of this invention, this lubricant layer 4 being formed on the surface of a magnetic layer 6 through the medium of a protective film 5, said magnetic layer 6 being formed on a non-magnetic support 7.

In both of the magnetic recording media shown in FIGS. 1 and 2, said lubricant layer, magnetic layer and protective film may be formed on both sides of the non-magnetic support.

DETAILED DESCRIPTION OF THE INVENTION

The present invention provides the fluorine-containing compounds having the terminal groups mentioned above in the molecule, of which some typical examples are shown below Examples of the aliphatic hydrocarbon terminal groups, namely aliphatic alkyl or alkenyl terminal groups include those having the following structural formulas:

$C_iH_{2i+1}-$,

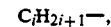

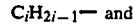

-continued $C_iH_{2i+1}-CH-C_kH_{2k}-$
$\phantom{C_iH_{2i+1}-CH}|$
$\phantom{C_iH_{2i+1}-}C_jH_{2j+1}$ wherein i and j are each an integer of 6 or greater, and k is 0 or an integer of 1 or greater. These terminal groups are recommended to be ones having 6-30 (preferably 10-26) carbon atoms. When the carbon number is less than 5 or greater than 31, the obtained lubricant is reduced in lubricity.

Examples of the fluoroalkylether terminal groups include those having the following structural formulae:

1

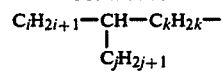

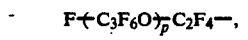

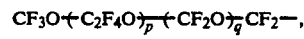

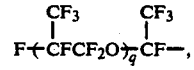

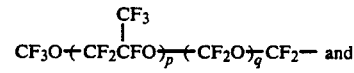 and

wherein p is an integer of 1 to 15, and q is an integer of 1 to 45. It is recommendable that these terminal groups be ones having 50 or less (preferably 40 or less) carbon atoms. If the carbon number is greater than 51, the effect of the polar terminal group is lessened.

A process for preparing the fluorine-containing compounds according to the present invention is described below.

The fluorine-containing compounds represented by the formula (1) can be produced by adding a tetrahydrofuran (THF) solution of a borane-THF complex to a THF solution of a fluorine-containing alkylamide ester and refluxing the mixture to reduce the carbonyl groups. The present inventors found that the fluorine-containing alkylamide esters used as starting materials of the fluorine-containing compounds according to this invention are capable of producing the single compounds with high purity and in a high yield owing to their high reactivity with the borane-THF complexes. This finding has made it possible to produce the fluorine-containing compounds of this invention at low cost and on an industrial scale.

The fluorine-containing alkylamide esters usable as starting materials for the preparation of the fluorine-containing compounds of this invention include those represented by the following formulae:

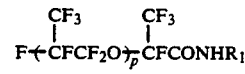

-continued

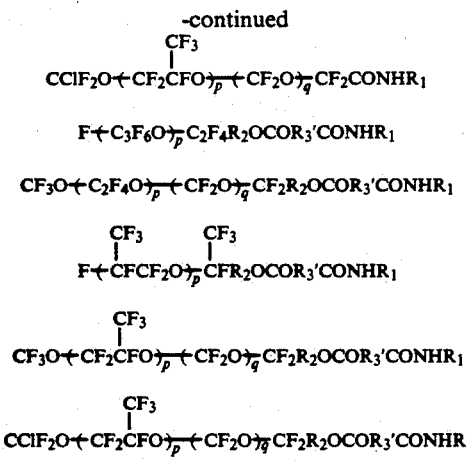

wherein $R_1$ represents an aliphatic alkyl or alkenyl terminal group; $R_2$ and $R_3$ represent an alkylene group; p is an integer of 1 to 15; and q is an integer of 1 to 45.

The lubricant composition of this invention preferably comprises a single fluorine-containing compound of the formula (1) or a mixture thereof with other lubricant(s). As other lubricants, it is preferred to use the fluorocarbon type lubricants, especially those disclosed in Japanese Patent Application Kokai Nos. 61-107527, 61-107528, 61-107529, 62-92225, 62 92226 and 62-92227. Other known lubricants and rust preventives can also be mixed as desired.

A fluorine-containing compound of the formula (1) needs to be contained in an amount of 20% or more, preferably 30% or more, in the lubricant composition according to this invention. If the content of said compound is less than 20%, the intended effect of the present invention can hardly be obtained.

A description is given here on typical examples of thin ferromagnetic metal film type magnetic recording media having a lubricant layer containing a fluorine-containing compound represented by the formula (1).

On the magnetic layer of a thin ferromagnetic metal film type magnetic recording medium, said lubricant composition is applied either directly or through the medium of a protective film by a usual wet application method or dry application method such as vacuum deposition. The lubricant composition is applied to form a thin coating layer on the surface of said magnetic layer at a coating weight of 0.05-100 mg/m$^2$, preferably 0.1-50 mg/m$^2$.

As material of the thin ferromagnetic metal film, there can be used Co, Co-Ni, Co-Cr, Co-Fe, Co-Ni-Cr, Co-Ni-Fe, Co-Ni-P, Co-Ni-Ta and the like or their partially oxidized versions. Said thin film can be formed by a suitable method such as vacuum deposition, sputtering, ion plating, plating, etc. If necessary, a prime coat of Cr, Ti or like material may be provided. The thickness of the ferromagnetic metal film including the prime coat is preferably in the range of 500-5,000 Å. On the surface of said ferromagnetic metal film, there may be formed as desired a metallic protective film of Cr, W, Ni-p alloy or the like, an inorganic protective film of SiO, SiC, carbon, graphite, diamond-like carbon or the like, an organic protective film of fluorine resin, silicone resin, epoxy resin, polyamide resin, plasma polymerization product, radiation polymerization product or the like, or a composite protective film.

As the non-magnetic support, there can be used basically glass, an oxide such as ceramic, a metal such as Al alloy and Ti alloy, or a plastic material such as polyester, polyimide, polyamideimide, polycarbonate, polyacrylate and the like. The surface of said non-magnetic support may be subjected to Co-P plating or polyimide coating or may be provided with protuberances of various forms such as lumpy, angular, undulant, etc., or those formed by texture working. As for the surface roughness of the support, its maximum roughness Rmax is preferably 50-600 Å. The shape of the support may be properly selected according to the form of the objective product such as tape, film, sheet, disc, card, drum, etc.

The fluorine-containing compounds of this invention have a fluoroalkylether terminal group, a aliphatic hydrocarbon terminal group and a specific polar group in the same molecule, and because of the appropriate molecular weight which is in the range of approximately 100-3,000, the effect of the polar terminal group is displayed to a well satisfactory degree and this polar group is allowed to adhere strongly to the surface of metal film or protective film and the surface of magnetic head. The fluoro-alkylether terminal group is exposed at the surface to contribute to energy reduction of the surface and serves for forming a non-adhesive face. The aliphatic hydrocarbon terminal group constitutes flexible carbon-carbon bond chains and is oriented by a moderate intermolecular action with the hydrocarbon chain of other adjoining molecule, so that it is conducive to betterment of compound lublicity.

Thus, the synergistic effect produced by said terminal groups realizes excellent lubricating performance of the compounds of this invention under all possible use conditions including harsh low-humidity environments and solves the problems relating to durability and reliability of the thin metal film type magnetic recording media.

As described above, the fluorine-containing compounds of this invention can be practically used as lubricants not only singly but also in the form of mixtures with other known compound(s). Further, they can be used for forming lubricant layers in the magnetic recording media. Thus, the compounds of this invention are of great industrial value.

DESCRIPTION OF PREFERRED EMBODIMENTS

Examples of the fluorine-containing compounds and the processes for preparing such compounds according to the present invention will be described in Examples 1-16 which follow, and examples of the magnetic recording media using the lubricant compositions containing said fluorine-containing compounds will be described in Examples 17-38. Mw represents molecular weight.

EXAMPLE 1

Preparation of a fluorine-containing compound having the following formula:

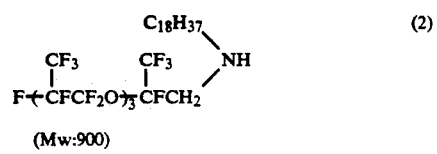

(Mw:900)

91.4 g (0.10 mol) of a fluorine-containing secondary alkylamide ester having the formula $F+(CF(CF_3)C-F_2O)_3-CF(CF_3)CO-NHC_{18}H_{37}$ and 300 ml of anhydrous tetrahydrofuran (THF) were supplied into a 1-liter flask equipped with an agitating element. Dried high-purity nitrogen was flown through the mixture for one minute and then 300 ml of a THF solution of 1 mol borane-THF complex was added dropwise to the mixture over a period of about 2 hours with stirring on a water bath of 15°-20° C. This was followed by 18-hour refluxing to complete the reaction. The reaction solution was cooled to 5°-10° C. and 100 ml of distilled water was added dropwise thereto carefully to perform hydrolysis. Then 50 ml of 6N hydrochloric acid was added and the reaction solution was heated to 85°-90° C. to evaporate away the THF in the atmosphere, after which 100 ml of 6N sodium hydroxide was added dropwise over a period of about one hour while continuing refluxing and stirring to isolate the amine. The resulting reaction mixture was prepared into a chloroform solution, and this solution was washed repeatedly with distilled water until the pH of the solution became 7, and then dried over anhydrous sodium sulfate. Then, after distilling off the chloroform, the reaction mixture was dissolved in benzene. This solution was cooled to 5° C. and the unreacted fluorine-containing secondary alkylamide ester was removed to obtain 50 g of a white solid matter having a melting point of 80° C. The results of infrared spectroscopic analysis (IR), gel permeation chromatographic analysis (GPC) and organic mass spectrometric analysis (FD-MS) of this white solid matter identified it as a fluorine-containing compound represented by the above shown formula (2) which contained no starting material nor any by-product.

IR: Absorption peak at 1640 cm$^{-1}$ due to carbonyl group disappeared.

GPC: No fluorine-containing secondary alkylamide ester used as starting material was detected.

FD-MS: Main peak was observed at m/e=890.

EXAMPLE 2

Preparation of a fluorine-containing compound of the following formula (3):

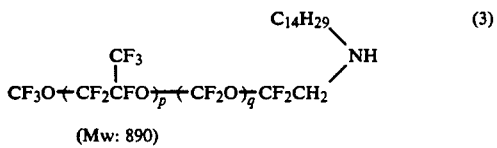

(Mw: 890)

90.4 9 (0.10 mol) of a fluorine-containing secondary alkylamide ester having the formula CF$_3$─[CF$_2$CF(CF$_3$)O]$_p$─[CF$_2$O]$_q$─CF$_2$CONHC$_{14}$H$_{29}$ (wherein p and q are each an integer of 1-9; Mw:904) and 300 ml of anhydrous THF were supplied into a one-liter flask equipped with an agitating element Dried high-purity nitrogen was made to flow through the mixture for one minute and then 300 ml of a THF solution of 1 mol borane-THF complex was added dropwise over a period of about 2 hours with stirring on a water bath of 15°-20° C. This was followed by 18-hour refluxing to complete the reaction. The reaction solution was cooled to 5°-10° C. and 100 ml of distilled water was added dropwise carefully to perform hydrolysis. Then 50 ml of 6N hydrochloric acid was added, the reaction solution was heated to 85°-90° C. to evaporate away THF in the atmosphere and 100 ml of 6N sodium hydroxide was added dropwise over a period of about one hour while continuing refluxing and stirring to isolate the amine. The resulting reaction mixture was subjected to the same purification treatment as conducted in Example 1 to obtain 54 g of a white solid with a melting point of 55° C. By IR, GPC and FD-MS, this white solid was determined to be a fluorine-containing compound of the above-shown formula (Formula 3) containing no starting material nor any by-product.

IR: Absorption peak at 1640 cm$^{-1}$ due to carbonyl group disappeared.

GPC: No fluorine-containing secondary alkylamide ester used as starting material was detected.

FD-MS: Main peak was observed at m/e=890.

EXAMPLES 3-8

The fluorine-containing compounds having the following structural formulae were produced according to the same procedure as Example 1.

Example 3:

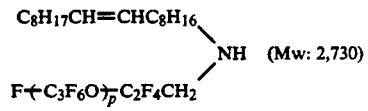

Example 4:

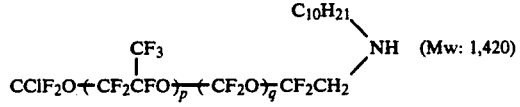

Example 5:

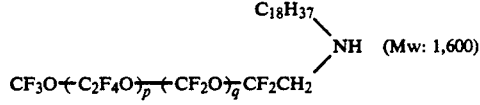

Example 6:

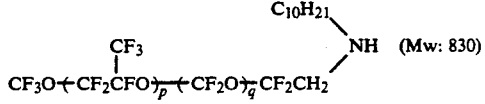

Example 7:

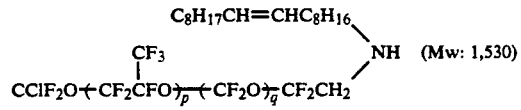

Example 8:

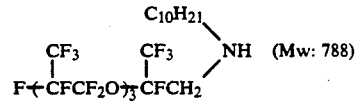

EXAMPLE 9

Preparation of a fluorine-containing compound having the following formula:

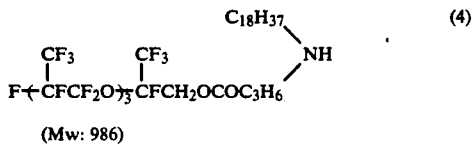

(Mw: 986)

100.0 g (0.10 mol) of a fluorine-containing secondary alkylamide ester having the formula F─[CF(CF$_3$)CF$_2$O]$_3$ CF(CF$_3$)─CH$_2$OCOC$_2$H$_4$CONHC$_{18}$H$_{37}$ and 300 ml of anhydrous THF were supplied into a one-liter flask equipped with an agitating element. Dried high-purity made to flow through the mixture for one minute and then 300 ml of a THF solution of 1 mol borane-THF complex was added dropwise over a period of about 2 hours with stirring on a water bath of 15°-20° C. This was followed by 18-hour reflux to complete the reaction. The reaction solution was cooled to 5°-10° C. and 100 ml of distilled water was added dropwise thereto carefully to perform hydrolysis. Then 100 ml of 3N hydrochloric acid was added and the reaction solution was heated to 85°-90° C. to evaporate away the THF in the atmosphere, after which 100 ml of 3N sodium carbonate was added dropwise over a period of about one hour while continuing refluxing and stirring to isolate the amine. The resulting reaction mixture was dissolved in chloroform and this solution was washed with distilled water repeatedly until pH of the solution became 7. Thereafter, the solution was dried over anhydrous sodium sulfate. Then the chloroform was distilled away and the reaction mixture was dissolved in benzene. This solution was cooled to 5° C. and the unreacted fluorine-containing secondary alkylamide ester (starting material) was removed to obtain 60 g of a white solid having a melting point of 90° C. By IR, GPC and FD-MS, this white solid was identified as a fluorine-containing compound having the above-shown formula (4) which contained no starting material nor any by-product.

IR: Absorption peak at 1640 cm$^{-1}$ due to carbonyl group disappeared.

GPC: The fluorine-containing secondary alkylamide ester used as starting material was not detected.

FD-MS: Main peak was present at m/e=986.

EXAMPLE 10

Preparation of a fluorine-containing compound represented by the formula:

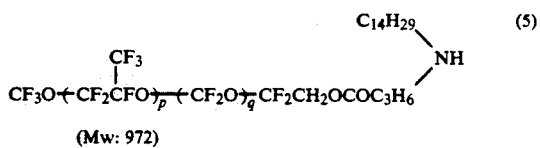

(5)

(Mw: 972)

98.6 g (0.10 mol) of a fluorine-containing secondary alkylamide ester represented by the formula CF$_3$O+CF$_2$CF(CF$_3$)O$\frac{1}{p}$+CF$_2$O+$_q$CF$_2$CH$_2$O-COC$_2$H$_4$CONHC$_{14}$H$_{29}$ (wherein p and q are each an integer of 1 to 9; Mw:986) and 300 ml of anhydrous THF were supplied into a 1-liter flask equipped with an agitating element. Dried high-purity nitrogen was flown through the mixture for one minute and then 300 ml of a THF solution of 1 mol borane-THF complex was added dropwise over a period of about 2 hours with stirring on a water bath of 15°-20° C. This was followed by 18-hour reflux to complete the reaction. The reaction solution was cooled to 5°-10° C. and 100 ml of distilled water was added dropwise thereto carefully to perform hydrolysis. Then 100 ml of 3N hydrochloric acid was added and the reaction solution was heated to 85°-90° C. to evaporate away the THF in the atmosphere, after which 100 ml of 3N sodium carbonate was added dropwise over a period of about one hour while continuing reflux and stirring to isolate the amine. The resulting reaction mixture was subjected to the same purification treatment as conducted in Example 1 to obtain 56 g of a white solid having a melting point of 65° C. IR, GPC and FD-MS identified this white solid as a fluorine-containing compound having the above-shown formula (5) which contained neither starting material nor any by-product.

IR: Absorption peak at 1640 cm$^{-1}$ due to carbonyl group disappeared.

GPC: No fluorine-containing secondary alkylamide ester used as starting material was detected.

FD-MS: Main peak was observed at m/e=972.

EXAMPLES 11-16

The fluorine-containing compounds having the following formulae were prepared according to the procedure of Example 9.

Example 11:

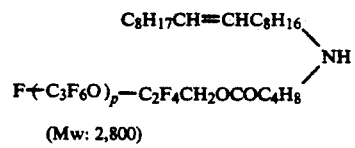

(Mw: 2,800)

Example 12:

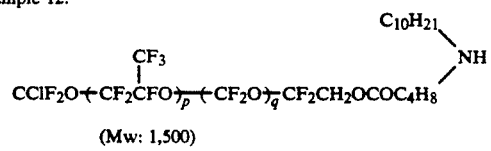

(Mw: 1,500)

Example 13:

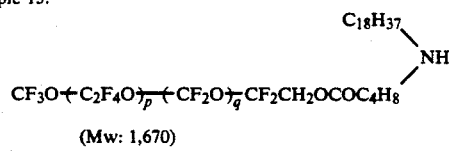

(Mw: 1,670)

Example 14:

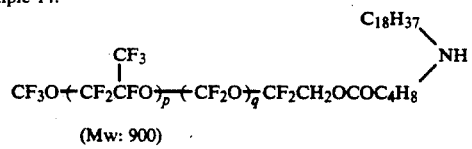

(Mw: 900)

Example 15:

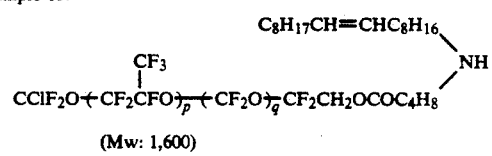

(Mw: 1,600)

Example 16:

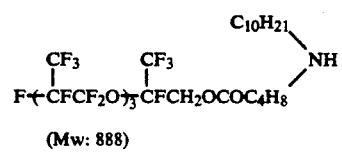

(Mw: 888)

EXAMPLE 17

There was prepared a polyester film in which the gentlesloping granular protuberances (average height: 70 Å, diameter: 1 μm) formed by the silica particles added into the film existed at a rate of several protuberances per 100 μm$^2$ on the surface and the relatively large protuberances due to the particles originating in the polymerization catalyst residue were minimized in number, and on the surface of this polyester film, the sharp cone-shaped protuberances created with 150 Å-diameter silica colloid particles as nucleus and an ultraviolet-curing epoxy resin as binder were formed at such a density that there would exist $1 \times 10^7$ protuberances per 1 mm$^2$, thereby obtaining a non-magnetic substrate. On this non-magnetic substrate was formed a ferro-magnetic metal (Co-Ni) film (Ni content: 20%, film thickness 1,000 Å) by a continuous vacuum slant deposition method in the presence of a slight amount of oxygen. The oxygen content in the film was 5 atom%.

On the thus prepared laminated films was formed a lubricant layer by applying severally the fluorine-containing compounds of this invention described above or the mixtures thereof with other known lubricants in such an amount that the compound or the mixture would exist at a rate of 10 mg per 1 m$^2$ of film surface, and the obtained laminates were cut to a predetermined size to make the magnetic tapes. Each of these tapes was set and run repeatedly in a commercial video deck under an environment of 23° C. and 5% RH. The output characteristics of each tape in repeated runs were determined, and the number of runs that each tape could endure until its RF output dropped 3 dB from the initial value or until a variation of output began to occur was counted. The results are shown in Table 1. The fluorine-containing compounds of this invention used in the test are indicated in Table 1 by the Example Nos. in which they were obtained. The results obtained with the tapes in which the lubricant layer was formed from a mixture of a fluorine-containing compound of this invention and a known lubricant and with the tapes in which the lubricant layer was formed from a known compound alone (Comparative Examples) are also shown in Table 1.

TABLE 1

| Magnetic tape | Compound of this invention (α) | Known lubricant (β) | α/β mixing ratio α:β | Number of times of repetitive run that tape endured |
|---|---|---|---|---|
| Example 18 | Example 1 | — | — | >200 |
| Example 19 | " | $C_7F_{15}C_2H_4$<br>$\phantom{xxx}$\>NH<br>$C_{14}H_{29}$ | 2:1 | >200 |
| Example 20 | Example 2 | — | — | >200 |
| Example 21 | " | $C_{17}H_{35}COOC_2H_4C_8F_{17}$ | 1:1 | >200 |
| Example 22 | Example 3 | — | — | >200 |
| Example 23 | Example 4 | — | — | >200 |
| Example 24 | Example 5 | — | — | >200 |
| Example 25 | Example 6 | — | — | >200 |
| Example 26 | Example 7 | — | 1:1 | >200 |
| Example 27 | Example 8 | — | — | >200 |
| Example 28 | Example 9 | — | — | >200 |
| Example 29 | " | $C_7F_{15}C_2H_4$<br>$\phantom{xxx}$\>NH<br>$C_{14}H_{29}$ | 2:1 | >200 |
| Example 30 | Example 10 | — | — | >200 |
| Example 31 | " | $C_{17}H_{35}COOC_2H_4C_8F_{17}$ | 1:1 | >200 |
| Example 32 | Example 11 | — | — | >200 |
| Example 33 | Example 12 | — | — | >200 |
| Example 34 | Example 13 | — | — | >200 |
| Example 35 | Example 14 | — | — | >200 |
| Example 36 | Example 15 | — | 1:1 | >200 |
| Example 37 | Example 16 | — | — | >200 |
| Comp. Example 1 | — | $C_7F_{15}C_2H_4$<br>$\phantom{xxx}$\>NH<br>$C_{14}H_{29}$ | — | 20 |
| Comp. Example 2 | — | $C_{17}H_{35}COOC_2H_4C_8F_{17}$ | — | 33 |
| Comp. Example 3 | — | $F\text{-}(CFCF_2O)_{\overline{p}}CF_2COOH$, with $CF_3$ branch (Mw: 2000) | — | 57 |
| Comp. Example 4 | — | $C_3F_7OCFCF_2OCFCONCH_2COOH$ with $CF_3$, $CF_3$, $CH_3$ branches | — | 50 |
| Comp. Example 5 | — | $C_3F_7OCFCF_2OCFCONCH_2COOH$ with $CF_3$, $CF_3$, $C_{12}H_{25}$ branches | — | 92 |

It is noted from Table 1 that the magnetic tape samples having a lubricant layer containing a fluorine-containing compound of this invention are all excellent in repetitive run durability in low humidity. In contrast, the magnetic tape samples having a lubricant layer made of a known lubricant alone are poor in durability in low humidity as shown in Comparative Examples.

EXAMPLE 38

The surface of a 1.2 mm thick, 95 mm-diameter Al alloy sheet was plated with a non-magnetic Ni-P alloy to a deposit thickness of 25 μm and formed with protuberances by texture working so that the average surface roughness would become 50 Å, the maximum height of the protuberances being 300 Å, thereby making a non-magnetic substrate. On this non-magnetic substrate were formed a 1,300 Å thick Cr prime coat and a 600 Å thick ferromagnetic metal film of Co-Ni by sputtering, followed by forming thereon a 200 Å thick graphite protective film by sputtering to prepare sample A. A similar laminate was prepared by following the above-described process except that a 50 Å thick diamond-like carbon protective film was formed by plasma CVD method instead of forming a graphite protective film. This preparation is referred to as sample B. On these samples, the fluorine-containing compounds of this invention or the mixtures thereof with other known lubricants were deposited at a rate of 10 mg per 1 $m^2$ of protective film surface, thereby forming a lubricant layer. The magnetic discs were made by properly cutting the obtained laminates. The magnetic discs were subjected to CSS durability test under the environment of 23° C. and 5% RH. Incidentally, "CSS durability test" is short for "contact start and stop durability test". In this test, a disc was set in a drive, thereafter the disc was made to rotate at 3,600 rpm for 2 seconds and then stopped. (It took 10 seconds to make the disc speed to reach 3,600 rpm and it took 30 seconds to stop the rotating disc.) This CSS operation was repeated 2,000 times and the disc was measured for coefficient of friction and the occurrence of head crush was checked. This procedure was repeated and the durability was judged by the number of repetitions of CSS that lasted until the moment when the coefficient of friction exceeded 0.1 or till the occurrence of head crush. The results are shown in Table 2. The fluorine-containing compounds of this invention used in the tests are indicated in Table 2 by the Example Nos. in which they were obtained. The results obtained with the discs in which the lubricant layer was formed from a mixture of a fluorine-containing compound of this invention and a known lubricant and with the discs in which the lubricant layer was formed from a known compound alone (Comparative Examples) are also shown in Table 2.

TABLE 2

| Magnetic disc | Compound of this invention (α) | Known lubricant (β) | α/β mixing ratio α:β | Sample type | Number of times of repetitive run that tape endured |
|---|---|---|---|---|---|
| Example 39 | Example 1 | — | — | A | >50,000 |
| Example 40 | " | $C_7F_{15}C_2H_4$<br>$\phantom{xxx}$>NH<br>$C_{14}H_{29}$ | 2:1 | B | >50,000 |
| Example 41 | Example 2 | — | — | B | >50,000 |
| Example 42 | " | $C_{17}H_{35}COOC_2H_4C_8F_{17}$ | 1:1 | A | >50,000 |
| Example 43 | Example 3 | — | — | A | >50,000 |
| Example 44 | Example 4 | — | — | A | >50,000 |
| Example 45 | Example 5 | — | — | A | >50,000 |
| Example 46 | Example 6 | — | — | A | >50,000 |
| Example 47 | Example 7 | — | — | A | >50,000 |
| Example 48 | Example 8 | — | — | A | >50,000 |
| Example 49 | Example 9 | — | — | A | >50,000 |
| Example 50 | " | $C_7F_{15}C_2H_4$<br>$\phantom{xxx}$>NH<br>$C_{14}H_{29}$ | 2:1 | B | >50,000 |
| Example 51 | Example 10 | — | — | B | >50,000 |
| Example 52 | " | $C_{17}H_{35}COOC_2H_4C_8F_{17}$ | 1:1 | A | >50,000 |
| Example 53 | Example 11 | — | — | A | >50,000 |
| Example 54 | Example 12 | — | — | A | >50,000 |
| Example 55 | Example 13 | — | — | A | >50,000 |
| Example 56 | Example 14 | — | — | A | >50,000 |
| Example 57 | Example 15 | — | — | A | >50,000 |
| Example 58 | Example 16 | — | — | A | >50,000 |
| Comp. Example 6 | — | $C_7F_{15}C_2H_4$<br>$\phantom{xxx}$>NH<br>$C_{14}H_{29}$ | — | A | Crushed in 5,000 times of CSS |
| Comp. Example 7 | — | $C_{17}H_{35}COOC_2H_4C_8F_{17}$ | — | A | Crushed in 5,000 times of CSS |
| Comp. Example 8 | — | $F\text{-}(CFCF_2O)_{\overline{n}}CF_2COOH$<br>with $CF_3$ branch<br>(Mw: 2000) | — | A | 10,000 |
| Comp. Example 9 | — | $C_3F_7OCFCF_2OCFCONCH_2COOH$<br>with $CF_3$, $CF_3$, $CH_3$ branches | — | A | 8,000 |

TABLE 2-continued

| Magnetic disc | Lubricant layer composition | | α/β mixing ratio α:β | Sample type | Number of times of repetitive run that tape endured |
|---|---|---|---|---|---|
| | Compound of this invention (α) | Known lubricant (β) | | | |
| Comp. Example 10 | — | CF₃ CF₃ C₁₂H₂₅<br>    \|     \|     \|<br>C₃F₇OCFCF₂OCFCONCH₂COOH | — | A | 20,000 |

It is seen from Table 2 that the magnetic disc samples having a lubricant layer containing a fluorine-containing compound of this invention are all excellent in CSS durability in low humidity. In contrast, the magnetic disc samples having a lubricant layer made of a known lubricant alone are poor in durability in low humidity as shown in the Comparative Examples.

What we claim:

1. A fluorine-containing compound represented by the formula:

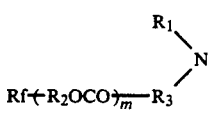

wherein Rf is a fluoroalkylether terminal group having 5–50 carbon atoms; $R_1$ is an aliphatic alkyl terminal group or an aliphatic alkenyl terminal group and has 10 or more carbon atoms; $R_2$ and $R_3$ are an alkenylene group; and m is 0 or 1.

2. A lubricant composition comprising a fluorine-containing compound represented by the formula

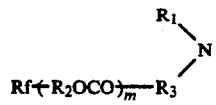

where Rf is a fluoroalkylether terminal group having 5–50 carbon atoms; $R_1$ is an aliphatic alkyl terminal group or an aliphatic alkenyl terminal group and has 10 or more carbon atoms; $R_2$ and $R_3$ are an alkenylene group; and m is 0 or 1.

3. A magnetic recording medium comprising a non-magnetic support, a ferromagnetic metal film formed on the non-magnetic support, a lubricant layer formed on the ferromagnetic metal film, and a protective film formed between the ferromagnetic metal film and the lubricant layer, the lubricant layer containing at least one fluorine-containing compound represented by the formula:

wherein Rf is a fluoroalkylether terminal group having 5–50 carbon atoms; $R_1$ is an aliphatic alkyl terminal group or an aliphatic alkenyl terminal group and has 10 or more carbon atoms; $R_2$ and $R_3$ are an alkenylene group; and m is 0 or 1.

* * * * *